Dec. 17, 1957 J. J. GRULLEMANS Plant Pat. 1,669
HEMEROCALLIS PLANT
Filed Jan. 14, 1957
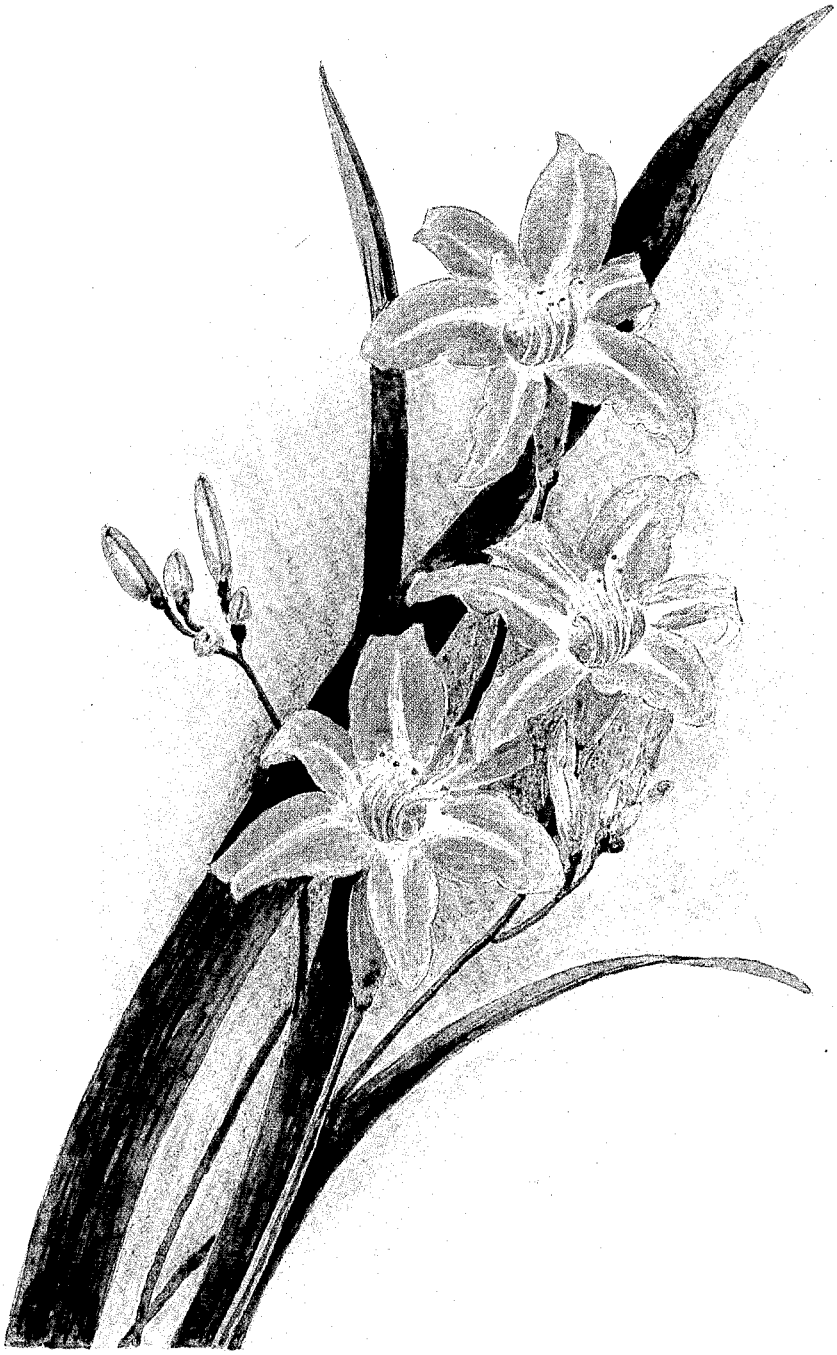
WITNESS
Addison E. Avery
INVENTOR
John J. Grullemans,
by:-
John H. Kouwenhoven,
his ATTY.

United States Patent Office

Plant Pat. 1,669
Patented Dec. 17, 1957

1,669

HEMEROCALLIS PLANT

John J. Grullemans, Harwichport, Mass.

Application January 14, 1957, Serial No. 634,135

1 Claim. (Cl. 47—60)

This invention relates to a new and distinct hybrid Hemerocallis plant.

The plant is illustrated in the drawing in which are shown a number of typical stems, blooms, buds, and leaves.

I obtained the seeds for the plant by crossing, as the parents, two unnamed Hemerocallis plants, each of which was a seedling. I obtained the seeds from which the parents were produced from unnamed hybrids which I had selected for color and which I was then growing specifically for breeding purposes in an experimental plot. I carefully controlled the pollination, and other factors affecting the growth, of the parent plants. I planted seeds produced by the crossing of these parents and selected one of the resultant seedlings, which grew to become the present plant.

The plant was first asexually reproduced by me at Mentor, Ohio, by plant division.

The plant has a tuberous to fibrous mass of roots which is usual, and of average size, for Hemerocallis plants. The roots have good resistance to wetness and drouth. Their winter resistance is good, both protected and unprotected. The plant has been grown without root damage in an open test field without protection for four years at Mentor, Lake County, Ohio, at a period during which the winter temperature reached as low as 10° below zero, Fahrenheit.

The roots seem to thrive well in a wide range of soil types.

The plant is an herbaceous and hardy perennial of generally upright and spreading growth. When grown, the exposed part of the plant is relatively dense and compact. It has the average height and spread for a three year old Hemerocallis plant which has been field grown. The exposed part of the plant is generally in the form of a symmetrical clump, generally rounded at the top.

The plant is vigorous in growth and its exposed parts withstand low temperatures well, both protected and unprotected, and also withstand well both drouth and wet seasons.

Its exposed portions have not been attacked by any diseases or insects.

For the best growth it prefers conditions varying from intense sunlight to partial shade in rather moist soil. It grows well in any of the soils ordinarily found in yards and gardens.

The main stalks or stems of the plant are curving. They are the usual length, stiffness, and toughness, and are generally adequate to support the bloom and fruit well. They have the usual color and surface texture.

The floral branches are of the usual surface texture and quantity, and are alternately arranged. They are stiff, but rather flexible, so that they support the bloom and fruit well. They are rather short for a Hemerocallis plant.

The color of the stems varies from a Peridot Green, comparable to Maerz and Paul Plate 22–L–6, to a green, comparable to Maerz and Paul Plate 22–L–8, with some yellow. The color is relatively uniform.

The foliage is dense and compact.

The leaves are basal and abundant and of the average size, length and width. They are linear from the base with entire margins and taper in the usual manner. They are of the average thickness and texture. Their persistency on the plant is good.

The plant produces an abundance of blooms of high quality throughout a geographical range in the United States from the east coast to the west coast, with but very few exceptions, and from Canada as far south as Florida. It produces the best blooms in the more temperate climates, however.

The blooms are produced to best advantage in full sunshine although an abundance of high quality blooms are produced in partial shade.

The best flowers are produced in a temperate moist season in soil which varies from moist to damp and from slightly acid to neutral. Though the best flowers are produced in a rich soil, the plant produces well throughout a wide range of soils.

The quality and quantity of the blooms are slightly reduced only if variations from the above normal ranges of conditions are very extreme.

The colors of the blooms are little affected by the growing conditions unless they become quite extreme.

The plant blooms continuously throughout late July and all of August.

The buds are of medium size and are of the usual plump and elongated shape for Hemerocallis plants. Their aspect is smooth and more or less waxy. They are borne generally upright on terminals of the stems. Their colors, based on the Ridgeway Color Charts, range from Indian Yellow, Plate 6/2, at the base to Light Turkey Red, during the period when the sepals first divide. When the petals begin to unfurl, they are of Light Turkey Red with slight yellow. When they are half blown, they are Turkey Red, with a slight tint of Cadmium Orange.

The sepals and calyx are of the usual size, shape and texture.

The peduncles vary in length from thirty-six to forty-two inches and are strong. They have the usual texture and color.

The pedicels or individual stalks of the blooms average from three to five inches in length and are strong. They have the usual texture and color.

The blooms range in size from about two and one half to two and three quarters inches in diameter. The average number of blooms at any given time within the blooming period ranges from fifteen to thirty or more for a single plant. They are borne in scapes of three to ten flowers each. They have the usual permanence on the plant and when cut. The color of the blooms based on the Ridgeway Color Charts ranges from a Cadmium Orange 8 to Cadmium at the center of the bloom and at the base of the petals. The outer portions of the petals are Turkey Red 721. On the inside of the blooms, the petals range from a Cadmium Orange 8 to Cadmium at the base, with a narrow band of the same color extending to approximately one half the length of the petal. The band then blends to Turkey Red 721 which is the dominant color of the petals.

The reverse of the petals ranges from Turkey Red with a cast of Cadmium.

The general tonality of the bloom of the plant from a distance is Turkey Red. There is little change in color during the blooming period.

The petals are of the usual texture, form and arrangement, being distinguished only by their color. The same is true of the bloom as a whole. The flower has a fragrance of the usual strength and quality.

The stamens range in color from Cadmium to Turkey Red. The filaments are relatively long. The color, they are Cadmium blend-to Turkey Red. There are usually about six stamens to the bloom.

The styles and stigmas are generally an Egyptian Buff with a slight Cadmium tint blending to Turkey Red.

Referring to the Maerz and Paul Dictionary of Color, the predominant color of the petals is a red varying from Plate 1–L–6 to Plate 3–L–6, to Plate 4–L–6.

The yellow streaks or bands range from Sunflower or Dandelion, Plate 9–L–4, ending in red, Plate 1–L–6, to Nugget Bronze Yellow, Plate 11–L-8 ending in red, Plate 4–L–6.

The stamens are red at the base, comparable to Plate 1–L–9 and pale yellow whitish at the tip.

The pistil is Sulphur Yellow or Citrus, comparable to Plate 10–J–1, with a whitish tip.

The fruit or seeds in general, are of the usual size and weight and general characteristics for Hemerocallis plants. They are borne in the usual manner of grouped bracts on scapes.

The outstanding feature of the plant is the unusual color of the blooms which is not found in blooms of other Hemerocallis plants.

Having shown and described my new variety of Hemerocallis plant and its mode of asexual reproduction, I claim:

The new and distinct variety of Hemerocallis plant as described and illustrated, distinguished particularly by the color of its blooms.

No references cited.